US00PP20053P2

(12) United States Plant Patent
Cole

(10) Patent No.: US PP20,053 P2
(45) Date of Patent: Jun. 2, 2009

(54) ***ARGYRANTHEMUM* PLANT NAMED 'ARCTIC BUTTERFLY'**

(50) Latin Name: *Argyranthemum frutescents*
Varietal Denomination: ARCTIC BUTTERFLY

(76) Inventor: Douglas Cole, 251 N. Village Rd., Loudon, NH (US) 03307

( * ) Notice: Subject to any disclaimer, the term of this patent is extended or adjusted under 35 U.S.C. 154(b) by 0 days.

(21) Appl. No.: 12/157,175

(22) Filed: Jun. 6, 2008

(51) Int. Cl.
*A01H 5/00* (2006.01)

(52) U.S. Cl. ..... Plt./406
(58) Field of Classification Search ..... Plt./406
See application file for complete search history.

*Primary Examiner*—Annette H Para

(57) ABSTRACT

A new and distinct *Argyranthemum frutescens* cultivar named 'Arctic Butterfly' is disclosed, characterized by white daisy type flowers having a diameter of at least 5 cm and a very well branched plant habit. The plant habit of the new variety is distinctive by producing more lateral branches than similar *Argyranthemum frutescens* with white ray florets. The new variety also produces more flowers in temperatures above 35° Celsius than similar *Argyranthemum frutescens*. The new variety is an *Argyranthemum frutescens,* and naturally blooms from Spring to early Fall.

1 Drawing Sheet

Figure 1:
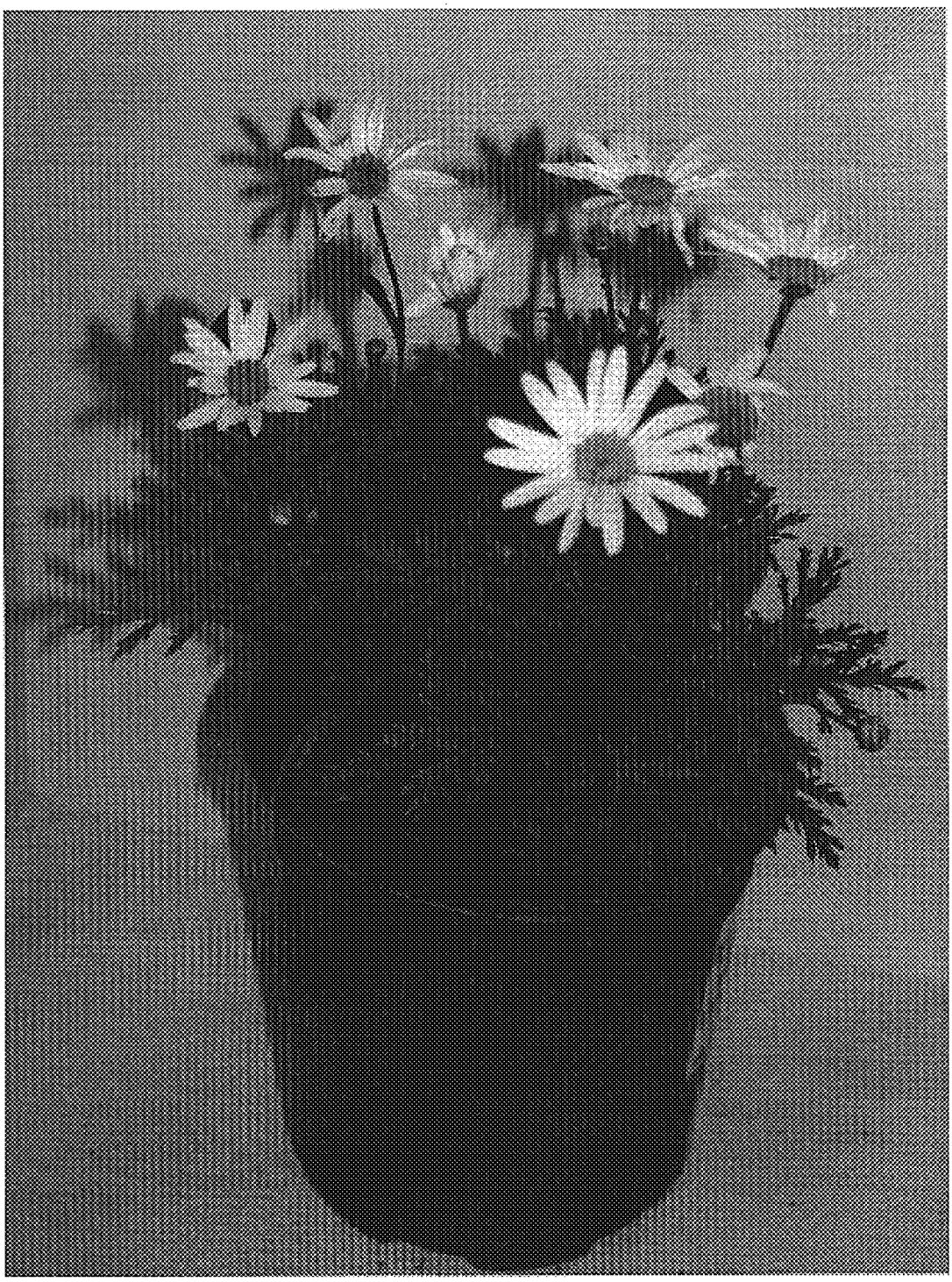

Latin name of the genus and species: *Argyranthemum frutescens.*
Variety denomination: 'ARCTIC BUTTERFLY'.

BACKGROUND OF THE INVENTION

The new variety was discovered, by the inventor, as a naturally occurring whole plant mutation in a grouping of more than 100 plants of the parent variety *Argyranthemum frutescens* 'Butterfly,' unpatented, in the United States. It was discovered by Douglas Cole in May 2003 at 251 North Village Road, Loudon, N.H., USA.

Asexual reproduction of the new cultivar 'Arctic Butterfly' by vegetative cuttings was performed in Loudon, N.H., USA beginning in June 2003 and has shown that the unique features of this cultivar are stable and reproduced true to type in successive generations. Approximately 10 generations have been reproduced.

SUMMARY OF THE INVENTION

The cultivar 'Arctic Butterfly' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Arctic Butterfly' These characteristics in combination distinguish 'Arctic Butterfly' as a new and distinct *Argyranthemum* cultivar:

1. The new variety has a more full growing habit than other white *Argyranthemums* used in pot production.
2. The new variety shows improved heat tolerance compared to other white *Argyranthemum* varieties. This includes higher flower production during the summer.
3. The new variety has longer ray florets than many of the white *Argyranthemum* varieties.

Plants of the new cultivar 'Arctic Butterfly' are similar to plants of the parent variety, *Argyranthemum frutescens*

'Butterfly,' in most horticultural characteristics; however, ray florets of the new cultivar 'Arctic Butterfly' are white, whereas the parent variety has yellow ray florets. Additionally, the new variety has narrower ray florets than the parent variety Plants of the new cultivar 'Arctic Butterfly' are similar to plants of the commercial variety 'Cobwhite,' U.S. Plant Pat. No. 17,103 in ray floret color. However, plants of the new cultivar 'Arctic Butterfly' differ in the following characteristics;

1. 'Arctic Butterfly' becomes larger in overall plant width during the growing season.
2. 'Arctic Butterfly' has a larger width inflorescence.
3. 'Arctic Butterfly' will continue to produce blooms at temperatures above 35° C. whereas 'Cobwhite' will stop producing blooms, or produce less than the new variety.
4. 'Arctic Butterfly' has longer ray florets.

Plants of the new cultivar 'Arctic Butterfly' are also similar to plants of the commercial variety 'Danarnep' U.S. Plant Pat. No. 13,719 in ray floret color. However, plants of the new cultivar 'Arctic Butterfly' differ in the following characteristics;

1. 'Arctic Butterfly' has a wider diameter inflorescence.
2. 'Arctic Butterfly' does not exhibit yellow foliage characteristic on new growth that 'Danarnep' often shows.
3. 'Arctic Butterfly' will continue to produce a consistent amount of blooms at temperatures above 35° C. whereas 'Darnarnep' will produce less blooms under similar conditions than the new variety.
4. 'Arctic Butterfly' has longer ray florets.

BRIEF DESCRIPTION OF THE PHOTOGRAPH

The accompanying photograph in FIG. 1 illustrates in full color a typical plant of 'Arctic Butterfly' grown in a greenhouse. The pot size is a commercial 1 gallon container, approximately 17 cm tall and 15 cm in diameter. The plant shown is approximately 20 weeks old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Arctic Butterfly' plants grown outdoors in Loudon, N.H. from March 2007 to June 2007. The growing temperature ranged from 15° C. to 16° C. at night to 15° C. to 32° C. during the day. Measurements and numerical values represent averages of typical flowering types.

Botanical classification: *Argyranthemum frutescens* cultivar 'ARCTIC BUTTERFLY.'

PROPAGATION

Time to rooting: 7 to 10 days at approximately 18° C.
Root description: Fine, fibrous.

PLANT

Growth habit: Mounding tender perennial.
Height: Approximately 21 cm.
Blooming period: Naturally blooming Spring to early Fall.
Plant spread: Approximately 25 cm.
Growth rate: Moderate to vigorous.
Branching characteristics: Free branching.
Length of lateral branches: Approximately 18 cm.
Diameter of lateral branches: Approximately 0.6 cm.
Quantity of lateral branches: Approximately 5 primary lateral branches, each with approximately 9 secondary lateral branches.
Texture of lateral branches: Smooth.
Color of lateral branches: Near RHS Yellow-Green 144 B.
Aspect: Upright.
Number of leaves per lateral branch: Approximately 18.
Age of plant described: Approximately 20 weeks from an unrooted cutting.

FOLIAGE

Leaf:
- *Arrangement.*—Alternate, simple.
- *Average length.*—Approximately 9.5 cm.
- *Average width.*—Approximately 3.7 cm.
- *Shape of blade.*—Pinnatifid, deeply dissected.
- *Apex.*—Acute.
- *Base.*—Attenuate.
- *Attachment.*—Stalked.
- *Margin.*—Entire, deeply and finely dissected.
- *Texture of top surface.*—Smooth.
- *Texture of bottom surface.*—Smooth.
- *Leaf internode length.*—Approximately 0.9 cm.
- *Color.*—Young foliage upper side: Near R.H.S. Green 143B. Young foliage under side: Near Green 143C. Mature foliage upper side: Near Green 137A. Mature foliage under side: Near Green 137C.
- *Venation.*—Type: Pinnate Venation color upper side: Near Yellow-Green 144A. Venation color under side: Near Yellow-Green 144B.

Petiole:
- *Average length.*—Approximately 4.0 cm.
- *Color.*—Near Yellow-Green 144B.
- *Diameter.*—Approximately 0.4 cm.

FLOWER

Bloom period: Naturally blooming from Spring to early Fall.
Bud:
- *Bud shape.*—Spherical.
- *Bud length.*—Approximately 0.6 cm.
- *Bud diameter.*—Approximately 0.6 cm.
- *Bud color.*—Near Green 143B.

Inflorescence:
- *Form.*—Single composite type daisy. Occurring on upright terminal and axillary peduncles.

Flower:
- *Diameter of entire flower.*—Approximately 5.5 cm.
- *Depth of flower.*—Approximately 1.6 cm.
- *Width of disc.*—Approximately 1.2 cm.
- *Depth of disc.*—Approximately 0.7 cm.

Ray florets:
- *Number of ray florets.*—Avg. 16.
- *Length.*—Approximately 2.5 cm.
- *Width.*—Approximately 0.4 cm.
- *Apex shape.*—Obtuse.
- *Margin.*—Entire.

Color:
Ray florets:
- *Upper surface at first opening.*—Near White N155A.
- *Upper surface at maturity.*—Near White N155A.
- *Upper surface at fading.*—Near White N155A.
- *Under surface at first opening.*—Near White N155A.
- *Under surface at maturity.*—Near White N155A.
- *Under surface at fading.*—Near White N155A.

Disc florets:
- *Number of disc florets.*—More than 200.
- *Length.*—Approximately 0.5 cm.
- *Width.*—Approximately 0.08 cm.
- *Shape.*—Cylindric.
- *Margin.*—Entire.
- *At first opening.*—Near Yellow-Orange 15B.
- *At maturity.*—Near Yellow-Orange 13A.
- *At fading.*—Near Yellow-Orange 15C.

Fragrance: None.

SEPAL

Number: Approximately 45.
Sepal length: Approximately 0.4 cm.
Sepal width: Approximately 0.2 cm.
Apex shape: Acute.
Margin: Entire.
Color: Inside sepal color near R.H.S. Yellow-Green 141C and outside sepal color near R.H.S. Yellow-Green 141C.

REPRODUCTIVE ORGANS

- *Androecium.*—Present on disc florets only. Stamens: 4. Anther length: Approximately 0.03 cm. Anther color: Near Yellow 13B. Pollen color: Near Yellow 17C.
- *Gynoecium.*—Present on ray and disc florets.

Ray florets:
- *Number of pistils per flower.*—1.
- *Stigma shape.*—Two parted.

*Stigma color.*—Near Yellow 12A.

*Style color.*—Near Yellow 4B.

*Style length.*—Approximately 0.2 cm.

Disc florets:

Ray florets:

*Number of pistils per flower.*—1.

*Stigma shape.*—Cylindric.

*Stigma color.*—Near Yellow 7A.

*Style color.*—Near Yellow 2C.

*Style length.*—Approximately 0.1 cm.

OTHER CHARACTERISTICS

Disease resistance: Neither resistance nor susceptibility to diseases or pests has been observed in this variety.

Drought tolerance and cold tolerance: Tender perennial. Hardy to 5° C. No drought tolerance has been observed.

Fruit/seed production: Fruit and seed production have not been observed in the new cultivar.

What is claimed is:

1. A new and distinct cultivar of *Argyranthemum* plant named 'Arctic Butterfly' as herein illustrated and described.

* * * * *